(12) United States Patent
Kishimori et al.

(10) Patent No.: US 6,336,358 B1
(45) Date of Patent: Jan. 8, 2002

(54) METHOD AND APPARATUS FOR MEASURING SEDIMENTATION RATE OF SEDIMENTS IN LIQUID SAMPLE

(75) Inventors: Shigenori Kishimori; Yoji Hasebe, both of Hirakata (JP)

(73) Assignee: Sefa Technology Inc., Osaka (JP)

( * ) Notice: Subject to any disclaimer, the term of this patent is extended or adjusted under 35 U.S.C. 154(b) by 0 days.

(21) Appl. No.: 09/572,316

(22) Filed: May 18, 2000

(30) Foreign Application Priority Data

May 19, 1999 (JP) ............................................ 11-139232

(51) Int. Cl.[7] .............................................. G01N 15/00
(52) U.S. Cl. ...................................... 73/61.65; 73/61.69
(58) Field of Search ............................. 73/61.65, 61.66, 73/61.69

(56) References Cited

U.S. PATENT DOCUMENTS

| | | | | |
|---|---|---|---|---|
| 4,495,975 A | * | 1/1985 | Harstrom et al. ............ | 141/157 |
| 4,566,315 A | * | 1/1986 | O'Brien et al. .............. | 73/61.4 |
| 5,133,208 A | * | 7/1992 | Ricci ......................... | 73/61.66 |
| 5,367,157 A | * | 11/1994 | Nilsson et al. ......... | 250/231.13 |
| 5,531,104 A | * | 7/1996 | Futterer et al. ............ | 73/61.69 |
| 5,565,977 A | * | 10/1996 | Rosinko ....................... | 356/39 |
| 5,779,983 A | * | 7/1998 | Dufresne et al. ........... | 422/102 |
| 5,827,746 A | * | 10/1998 | Duic .......................... | 436/70 |
| 5,844,128 A | * | 12/1998 | Bull ........................... | 73/61.66 |
| 5,891,314 A | * | 4/1999 | Heffelfinger et al. ...... | 204/461 |
| 6,098,451 A | * | 8/2000 | Bull ........................... | 73/61.66 |

* cited by examiner

Primary Examiner—Hezron Williams
Assistant Examiner—C D Garber
(74) Attorney, Agent, or Firm—Rader, Fishman & Grauer, PLLC

(57) ABSTRACT

A measuring technology of sedimentation rate of sediments in a liquid sample capable of measuring, for example, the sedimentation rate of erythrocytes in a patient requiring an urgent medical treatment in about ¼ of the time needed in the conventional measuring method, and also capable of measuring the sedimentation rate of erythrocytes in an infant limited in the blood sampling volume. A test container filled with a liquid sample is inclined and held at a specific inclination angle, light is projected to this test container, the light passing through the test container is electrically detected by a line sensor or the like, the liquid level of the supernatant in the liquid sample and the position of the boundary of the supernatant and sediments are calculated to obtained the depth of the sediments, and the sedimentation rate of the sediments is calculated from the depth of the sediments and the measuring time.

15 Claims, 6 Drawing Sheets

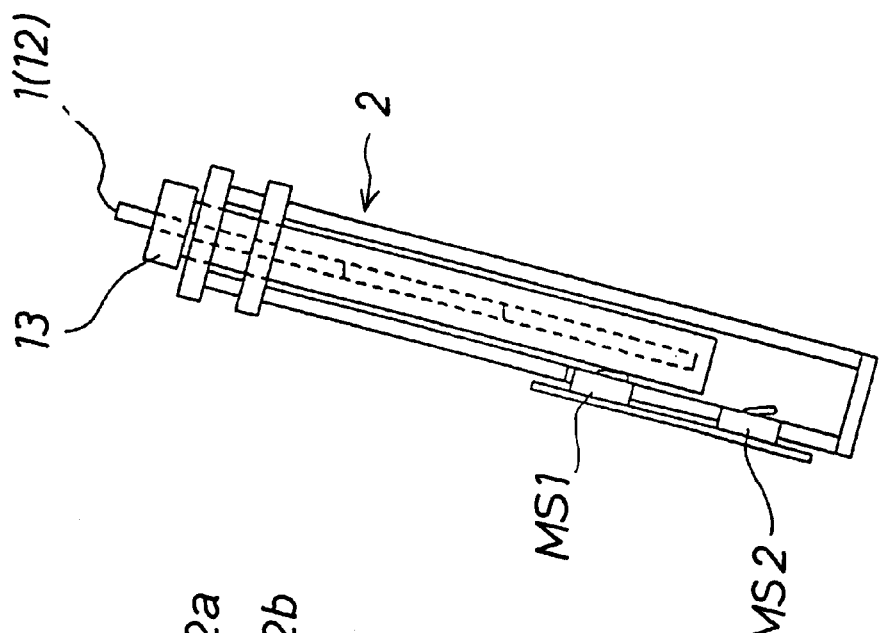
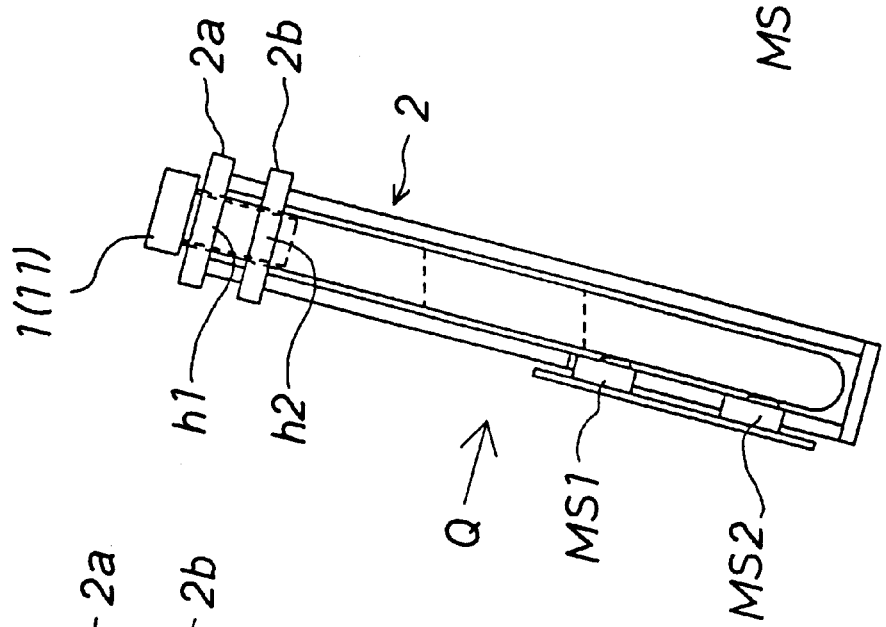
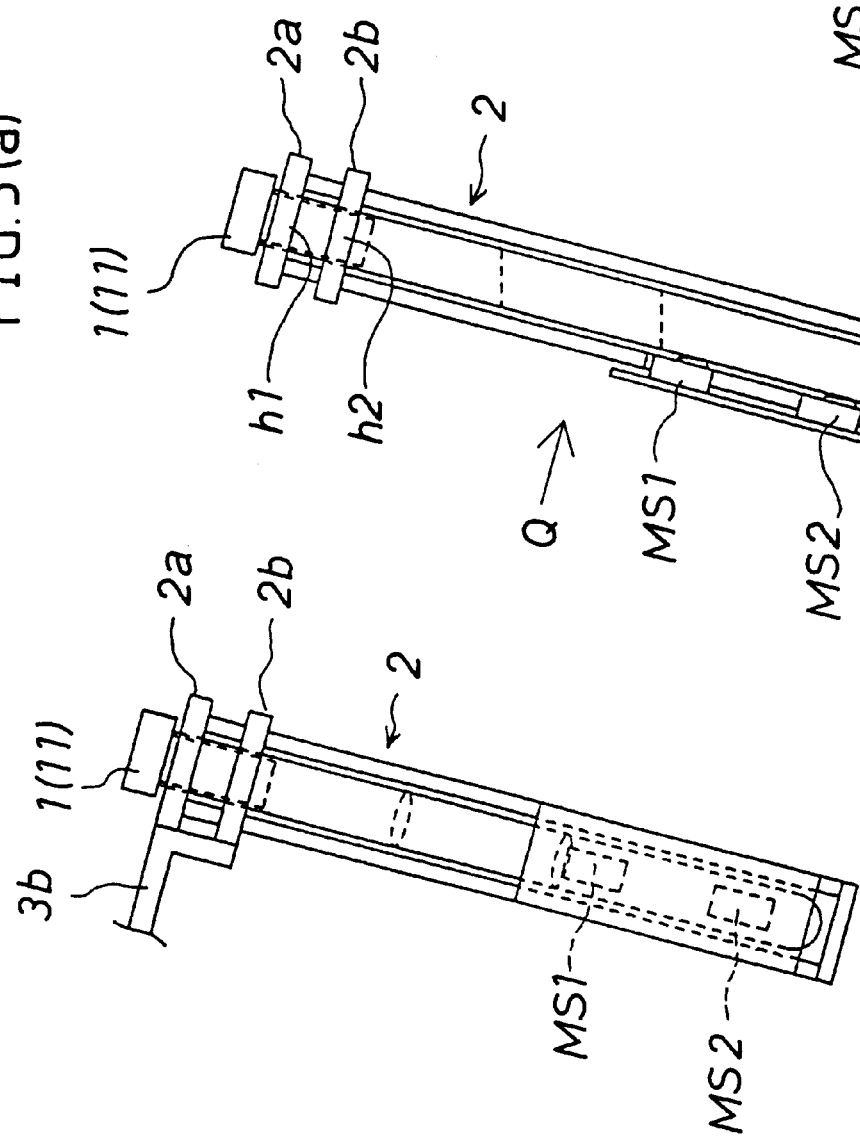

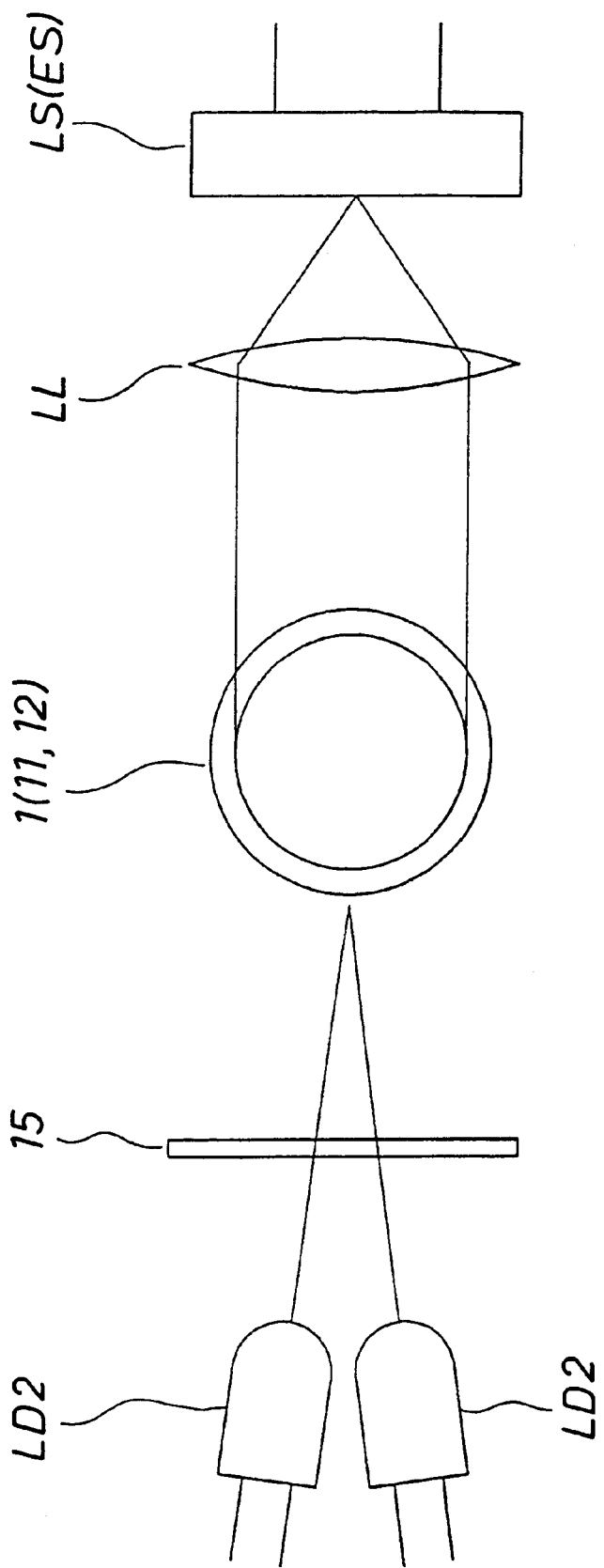

METHOD AND APPARATUS FOR MEASURING SEDIMENTATION RATE OF SEDIMENTS IN LIQUID SAMPLE

BACKGROUND OF THE INVENTION

1. Field of the Invention

The present apparatus relates to a measuring method of sedimentation rate of sediments in a liquid sample, and its apparatus, and more particularly to the technology for measuring optically the sedimentation rate of sediments in a liquid sample contained in a test tube or other transparent container.

2. Description of the Related Art

A typical example of measurement of sedimentation rate of sediments in a liquid sample is measurement of sedimentation rate of erythrocytes which is one of the most common clinical examinations. As the measuring method of erythrocyte sedimentation rate, the Westergren method is employed as a standard technique. In the Westergren method, a specific blood sampling tube held in vertical position is filled with nonclotting blood and let stand, and the height of the blood cell layer caused by sedimentation of erythrocytes (sedimentation height of erythrocytes) is recorded by a laboratory technician in one hour after letting stand, then the speed of sedimentation of erythrocytes is judged.

In this measuring method, however, it takes at least one hour from start till end of measurement, and it is not suited in case of emergency.

The blood sampling tube used as a test container in the Westergren method is a glass tube of 2.55 mm in inside diameter, and 300 mm in overall length, and to fill this blood sampling tube with 1 part of sodium citrate solution as coagulant and 4 parts of blood by volume, about 2 cc of blood is needed, and it is not suited to hematological examination of infants essentially small in the allowable blood sampling volume.

SUMMARY OF THE INVENTION

It is hence an object of the invention to present a novel technology for measuring the sedimentation rate by solving the problems of the prior art.

It is other object of the invention to present a measuring method of sedimentation rate capable of measuring the sedimentation rate of liquid sample containing sediments accommodated in a test container, accurately in a short time, even if the sample is a small amount of liquid, by using optical means.

It is another object of the invention to present a measuring apparatus of sedimentation rate for executing this measuring method.

The measuring method of sedimentation rate of the invention comprises the steps of holding a test container accommodating a liquid sample containing sediments at a specified inclination angle so as to produce a natural convection to promote sedimentation of the sediments in the liquid sample, projecting light to the test container, detecting the light passing through the test container electrically, and calculating the depth of supernatant in the liquid sample from the time-course changes of this detected value so as to measure the sedimentation rate of the sediments.

A first constitution of the measuring apparatus of sedimentation rate of the invention comprises inclination holding means for holding a test container accommodating a liquid sample containing sediments in an inclined state, projecting means for projecting light to the test container, photo detecting means disposed oppositely to the projecting means across the test container, for detecting the light passing through the test container from the projecting means, and converting photoelectrically, light quantity change measuring means for measuring time-course changes of the photo detecting means output, and sedimentation rate calculating means for calculating the sedimentation rate of sediments in the test container on the basis of the result of measurement by the light quantity change measuring means.

A second constitution of the measuring apparatus of sedimentation rate of the invention comprises a plurality of inclination holding means for holding a plurality of test containers accommodating liquid samples containing sediments in an inclined state, a turntable on which the plurality of inclination holding means are disposed on the circumference, being supported rotatably about its central axial line, rotation driving means for rotating and driving this turntable, for indexing and stopping one of the test containers so as to be positioned at the measuring position, projecting means for projecting light to the test container positioned at the measuring position, photo detecting means disposed oppositely to the projecting means across this test container, for detecting the light passing through the test container from the projecting means, and converting photoelectrically, light quantity change measuring means for measuring time-course changes of the photo detecting means output, control means for controlling this light quantity change measuring means and the rotation driving means in synchronism, and sedimentation rate calculating means for calculating the sedimentation rate of sediments in the test container on the basis of the result of measurement by the light quantity change measuring means.

Preferably, the inclination holding means is, for example, for use in measurement of sedimentation rate of erythrocytes, designed to incline and hold two kinds of test containers, that is, standard test container (standard tube) and fine test container (capillary tube), and includes detecting means for detecting which one of the two test containers has been inserted.

As in the invention, when the test container filled with liquid sample containing sediments is held in an inclined state, the sedimentation rate of the sediments is promoted by natural convection. By sedimentation of the sediments, a boundary of supernatant and sediments appears in the test container, and this boundary descends with the passing of the time, and descent of the boundary stops at a certain time (sedimentation of sediments stops).

The quantity of light passing through this liquid sample changes with the clarity (corresponding to the content) of the test container (transparent container), and the light passing through the space above the supernatant (space free from liquid sample), the light passing through the supernatant, and the light passing through the sediments can be clearly distinguished. Hence, by detecting the change of the transmitted light quantity, the liquid level of the supernatant, and the boundary of the supernatant and sediments can be securely discriminated.

Therefore, by detecting the changes of quantity of light passing through the test container electrically by means of CCD the line sensor, photo diode array, CCD area sensor, or other photo detectors, the depth of the supernatant is calculated from the time-course changes of these detected values. As a result, from the calculated value and the measuring time, the sedimentation rate of sediments can be calculated.

For example, when measuring the sedimentation rate of erythrocytes by using a mixed solution of 1 part of sodium citrate solution and 4 parts of blood by volume, the quantity of light changes significantly when passing through the boundary of sediments or blood cell layer (clotting sediments of erythrocytes and other corpuscles) and supernatant or plasma, and the boundary of the plasma and space free from mixed solution, that is, the liquid level of plasma, and by detecting this change of quantity of light by CCD line sensor, photo diode array, CCD area sensor or the like, the time-course changes of plasma depth can be detected in real time, and the maximum depth can be calculated, so that the sedimentation rate of erythrocytes can be determined.

In this measurement of sedimentation rate of erythrocytes, by holding the test container in an inclined state, the sedimentation rate of erythrocytes is promoted by natural convection, and the sedimentation rate of erythrocytes can be measured in a short time.

This promoting effect of sedimentation rate of erythrocytes by holding the test container in an inclined state is the same if the test container is a fine tube (capillary tube), and therefore in babies and infants small in the allowable blood sampling volume, the sedimentation rate of erythrocytes can be measured safely, promptly, and accurately.

These and other objects and features of the invention will be better understood and appreciated from reading of the detailed description together with the accompanying drawings and novel facts disclosed in the claims.

BRIEF DESCRIPTION OF THE DRAWINGS

FIG. 3(a) is a schematic view of inclination holding means in embodiment 1, in arrow P view of FIG. 2 using standard tube as test container.

FIG. 3(b) is also a schematic view of inclination holding means in embodiment 1, in arrow P view of FIG. 2 using capillary tube as test container.

FIG. 3(c) is an arrow Q view of FIG. 3(a).

FIG. 6 is a plan view showing an example of a relative configuration of projecting means, test container, and receiving means, in a measuring apparatus of sedimentation rate capable of measuring serum color in embodiment 2 of the invention.

DETAILED DESCRIPTION OF THE PREFERRED EMBODIMENTS

Figure 1:
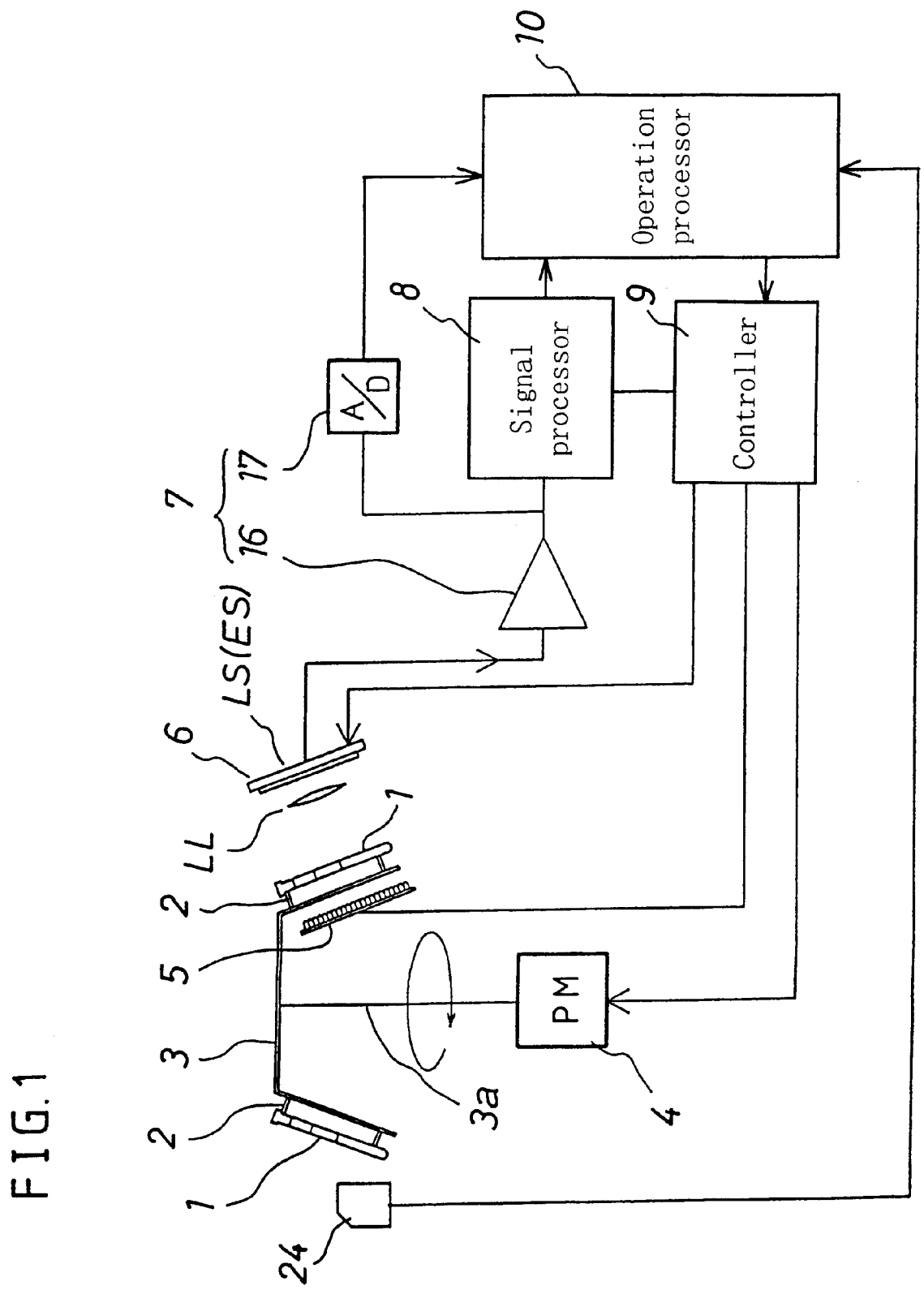
FIG. 1 is a block diagram showing an outline of measuring apparatus of sedimentation rate in embodiment 1 of the invention.

Referring now to the drawings, preferred embodiments of the invention are described in detail below.

FIG. 1 to FIG. 6 show the measuring apparatus of sedimentation rate according to the embodiments of the invention, and same reference numerals throughout the drawings indicate same components or elements.

EMBODIMENT 1

FIG. 1 shows a measuring apparatus of sedimentation rate of the invention. This apparatus, specifically, measures the sedimentation rate of erythrocytes in the blood contained in a blood sampling tube which is a test container as shown in FIG. 3. The apparatus mainly comprises a turntable 3 on which eight blood sampling tube holders 2, 2, . . . disposed on the circumference as the inclination holding means for holding a plurality of (eight in this embodiment) blood sampling tubes 1, 1, . . . in an inclined state, preferably at an inclination angle of 15 to 25 degrees; a pulse motor (pulse motor with reduction gear) 4 which is rotation driving means coupled to a rotary shaft 3a of this turntable 3, for rotating the turntable 3 and stopping at measuring position; projecting means 5; photo detecting means 6; position detecting means 7 for detecting the stopping position of the turntable 3; a signal processor 8 which is means for measuring changes in the quantity of light; a controller 9 as control means; and an operation processor 10 as calculating means of sedimentation rate.

The blood sampling tube holder 2 is for holding the blood sampling tube 1 filled with sampled tube in an inclined state, and a plurality (eight in the shown example) are disposed on the circumference of the turntable 3 at equal intervals in the circumferential direction.

Figure 2:
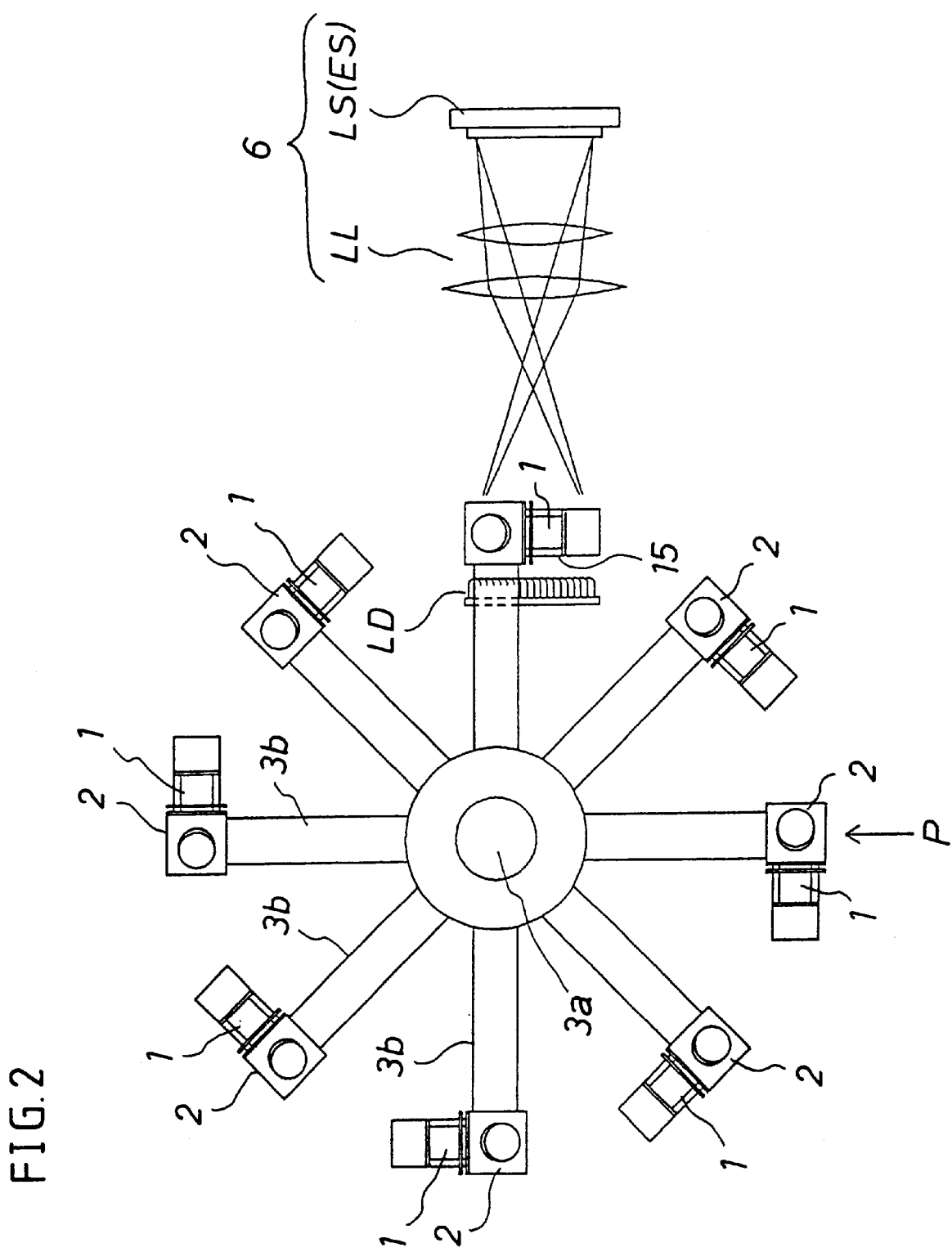
FIG. 2 is a plan view showing a relative configuration of projecting means, inclination holding means, and photo detecting means in embodiment 1.
Figure 4:
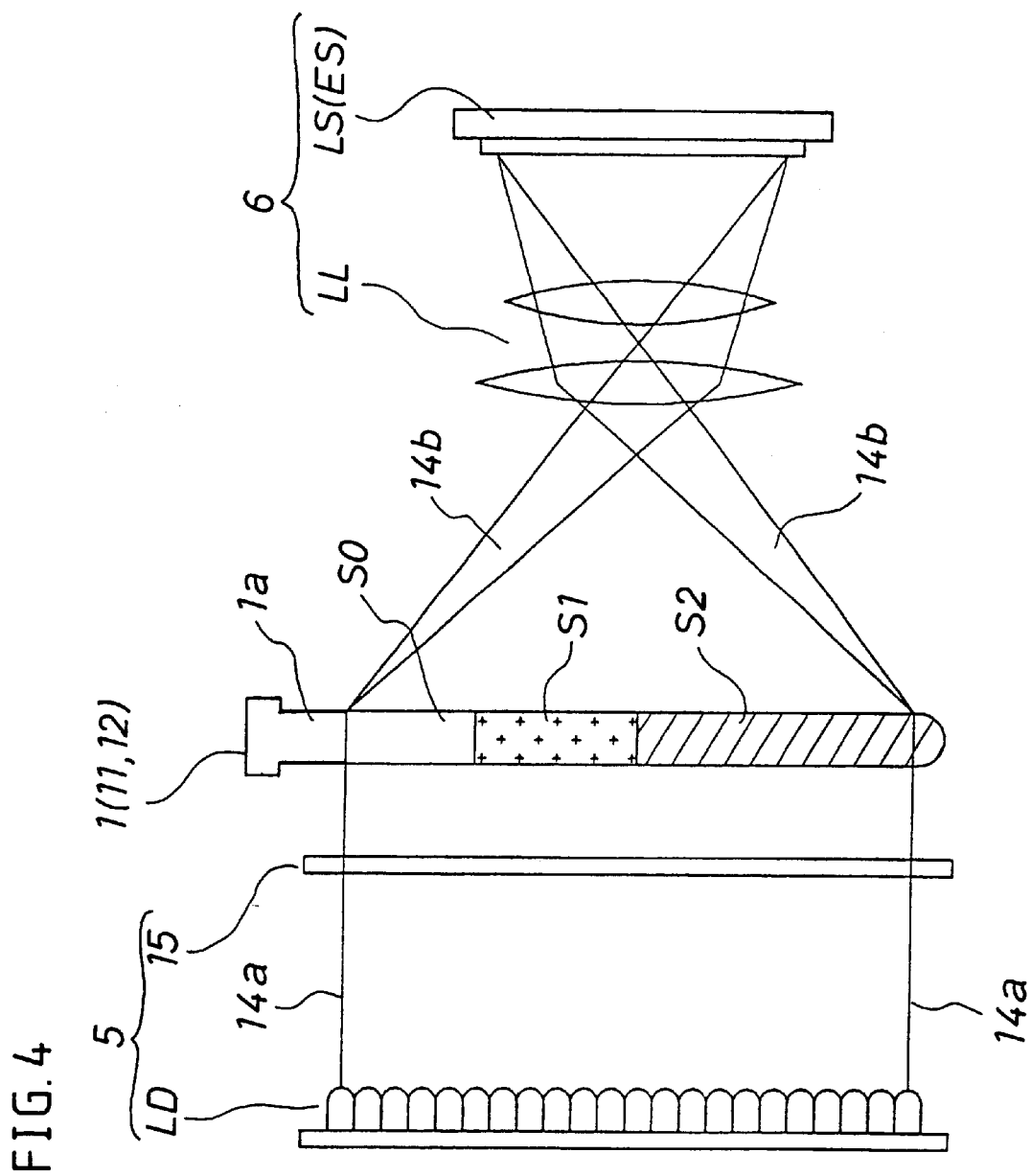
FIG. 4 is a side view showing an example of a relative configuration of projecting means, tests container, and photo detecting means in embodiment 1.

That is, the turntable 3 has eight ribs 3b, 3b, . . . extending radially at the leading end of the rotary shaft 3a as shown in FIG. 2, and at the leading end of each rib 3b, the blood sampling tube holder 2 is mounted and fixed at a specified inclination angle to the circumferential direction, preferably, at an inclination angle of 15 to 25 degrees.

In FIG. 1, the inclination direction of the blood sampling tube holders 2, 2, . . . is shown in the direction parallel to the sheet of paper, it is for the purpose of convenience of explanation of the inclined state of the blood sampling tube holder 2, and actually it is inclined in the direction at right angle to the sheet of paper.

The blood sampling tube holder 2 is specifically a skeleton tube made of resin material or the like as shown in FIG. 2 and FIG. 3. Round holes h1, h2 are formed in an upper plate 2a of this blood sampling holder 2, and a middle plate 2b disposed slightly below the upper plate 2a. These round holes h1, h2 have a structure of inclining and holding both a standard tube 11 which is a blood sampling tube used in measurement of sedimentation rate of erythrocytes in adults, and a capillary tube 12 which is a blood sampling tube used in measurement of sedimentation rate of erythrocytes in infants.

The round holes h1, h2 are designed corresponding to the shape and size of the standard tube 11, and the standard tube 11 is directly inserted and held, while the capillary tube 12 is held through a capillary holder 13. The inside diameter and shape of the capillary holder 13 are designed corresponding to the outside diameter of the capillary tube 12, and its outside diameter and shape are designed corresponding to the outside diameter of the standard tube 11.

These two kinds of blood sampling tubes 1 (11, 12) can be a detected and distinguished by two microswitches MS1 and MS2 provided as detecting means at the lower left side of the blood sampling tube holder 2. That is, when the both microswitches MS1 and MS2 are ON, it is judged that the standard tube 11 is CCE used as the test container or the blood sampling tube, and when the microswitch MS1 is ON and MS2 is OFF, it is judged that the capillary tube 12 is used as the blood sampling tube.

In this constitution, the sedimentation rate of erythrocytes can be measured by plural blood sampling tubes 1 differing in shape and size.

The projecting means 5 projects light (projection light) 14a to the blood sampling tube 1 positioned at measuring position and filled with sampled blood. The projecting means 5 comprises a light source LD, and a scatter board 15 for emitting the projection light 14a from the light source LD uniformly to the blood sampling tube 1. In this embodiment, the scatter board 15 is provided at the back side of the blood sampling tube holders 2, 2, . . . (see FIG. 2 and FIG. 3 (c)).

As the light source LD, an LED (light emitting diode) array, or preferably a red LED array is used, and this light source LD and the scatter boards 15, 15, . . . are set at the same inclination angle as the inclination angle of the blood sampling tube 1.

The photo detecting means 6 is to detect the light passing through the blood sampling tube 1 at the measuring position from the projecting means 5, and convert photoelectrically. The photo detecting means 6 is disposed oppositely to the projecting means 5 across the blood sampling tube 1. Specifically, the photo detecting means 6 comprises a line sensor LS such as CCD line sensor or photo diode array disposed oppositely to the projecting means 5 across the blood sampling tube 1, and an objective lens LL for converging the light 14b from the light source LD passing through the blood sampling tube 1 on the line sensor LS.

The position detecting means 7 is means for stopping the turntable 3 accurately at the measuring position of the blood sampling tube 1, and is mainly composed of an analog amplifier 16 and an A/D converter 17, and the photoelectric conversion output V of the line sensor LS is used in detection.

Figure 5:
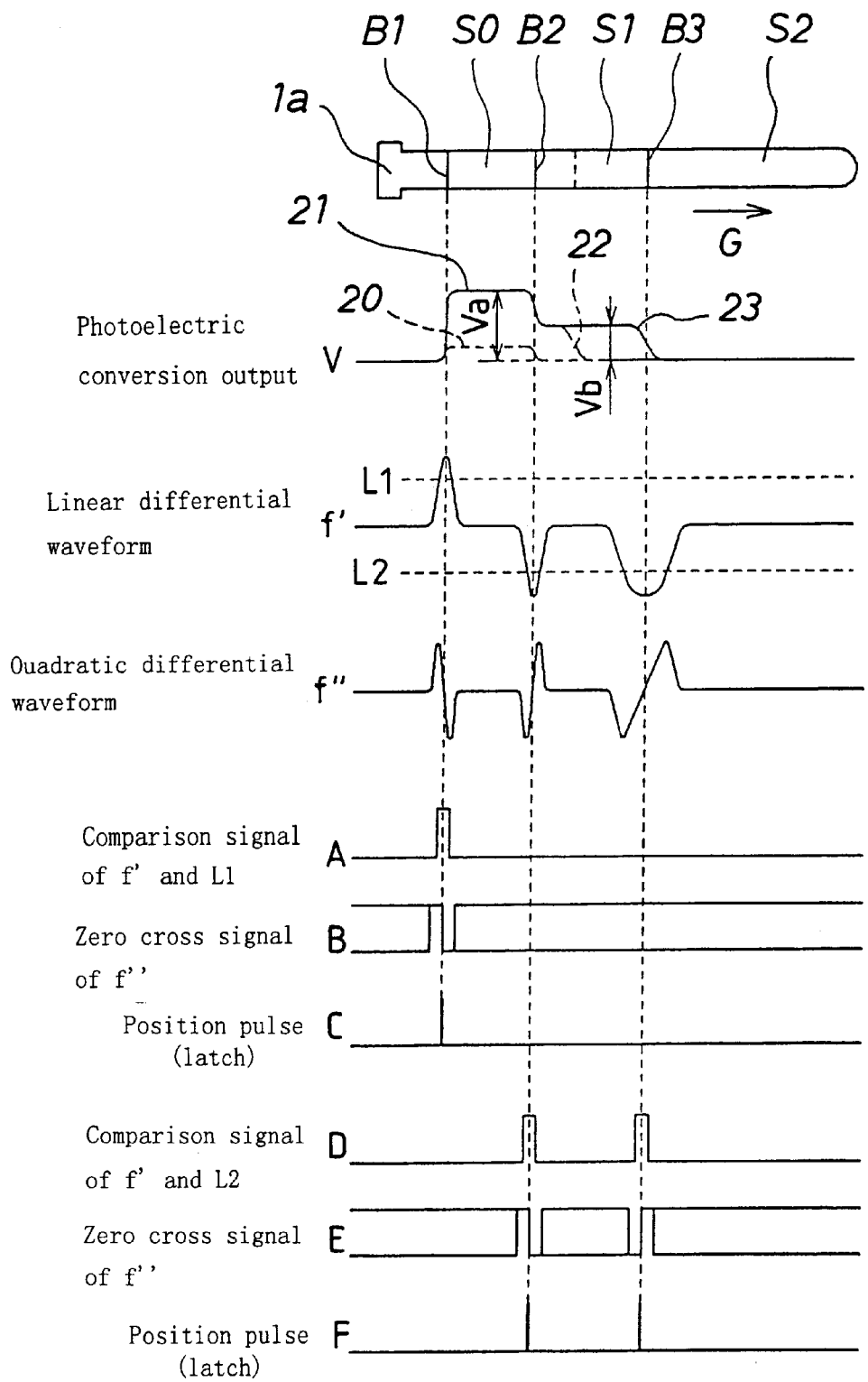
FIG. 5 is a line diagram showing the quantity of line light (photoelectric conversion output) of transmitted light when the projected light passes through the space in the test container, in the plasma (supernatant), and in the blood cell layer (sediments), and the signal processing waveform in the signal processing unit.

The photoelectric conversion output V of the line sensor LS varies with the transmission quantity of light corresponding to the blood or the content in the blood sampling tube 1 as shown in FIG. 5. That is, the transmission quantity in the space S0 free from sample is the greatest expressed by Va. Then the transmission quantity through the sample S1 (plasma) is damped by the presence of the plasma and is lowered to Vb. The transmission quantity through the sample S2 (blood cell layer) is damped almost completely by the presence of corpuscles and is nearly 0.

The position detecting means 7 makes use of this photoelectric conversion output Va. That is, when measuring the sedimentation rate of erythrocytes in a certain blood sampling tube 1, simultaneously with start of measurement, the turntable 3 begins to rotate, and when the blood sampling tube 1 approaches the measuring position, the light from the LED array LD begins to pass through the space S0 in the blood sampling tube 1, and a slight photoelectric conversion output Va (broken line 20 in FIG. 5) from the line sensor LS is detected.

This photoelectric conversion output Va is A/D converted in the A/D converter 17, and is taken into the operation processor 10. As a result, a slow-down command of the pulse motor 4 is given to the controller 9, and the turntable 3 is changed from the normal speed mode to the low speed mode.

When the turntable 3 slows down, the photoelectric conversion output Va increases gradually until reaching the maximum value (broken line 21 in FIG. 5), and then decreases, and finally becomes 0 when the blood sampling tube 1 is away from the measuring position. The value of photoelectric conversion output Va max at this time is stored in the operation processor 10.

In succession, a speed-up command of the pulse motor 4 is given to the controller 9, and the turntable 3 returns to the normal speed mode from the low speed mode, and the blood sampling tube 1 approaches the measuring position again, and the turntable 3 slows down, and the photoelectric conversion output Va changes similarly in the time course as mentioned above. The value of the photoelectric conversion output Va at this time, and the previously stored value of photoelectric conversion output Va max are compared in the slow speed mode in the operation processor 10, and when Va is equal to or smaller than Va max, a stop command of the pulse motor 4 is given to the controller 9, so that the turntable 3 is stopped.

The signal processor 8 measures time-course changes of the output of the photo detecting means 6. Specifically, the signal processor 8 detects the photoelectric conversion output V of the line sensor LS, and measures the time-course changes. This output changes corresponds to the content in the blood sampling tube 1 as mentioned above, and is, for example, as shown in FIG. 5, in which Va denotes the received quantity of the light transmitting the space S0, and Vb is the received quantity of the light passing through sample 1 (plasma). The light hardly passes through sample 2 (blood cell layer), and it is 0.

The photoelectric conversion output V changes en significantly at the end of the blood sampling tube 1, in this embodiment, boundary B1 of cap 1a and space S0, boundary B2 of space S0 and plasma S1, and boundary B3 of plasma S1 and corpuscle S2.

Of these boundaries, the phase of boundary B1 and B2 is not changed in the same blood sampling tube, and only boundary B3 is changed. That is, upon start of measurement, boundary B3 does not exist, but a short while after start of measurement, aggregates of erythrocytes sediment and begin to collect, and as the time passes, boundary B3 is formed, and it moves downward (see arrow G in FIG. 5), and a change occurs in the photoelectric conversion output Vb at the position indicated by 22.

As the sedimentation further advances, at an optimum timing for measurement of sedimentation rate of erythrocytes, the boundary B3 is moves to the position of 23 in FIG. 5. The photoelectric conversion output Vb at this time is nearly equal to the photoelectric conversion output Vb when the boundary B3 at the position of 22.

The signal processor 8 processes the photoelectric conversion outputs Va and Vb at these three boundary positions, and sends out the position pulse (latch signal) to the operation processor 10.

That is, by linear differentiation of photoelectric conversion output V (Va and Vb), the linear differential waveform f' is obtained, and further by quadratic differentiation, a quadratic differential waveform f" is obtained.

Later, by comparison between the linear differential waveform f' and set value L1, clipping signal A is obtained, and similarly by comparison between the linear differential waveform f' and set value L2, clipping signal D is obtained. On the other hand, from the quadratic differential waveform f", zero cross signals B and E are obtained.

Further, by comparison between the clipping signal A and zero cross signal B, position pulse (latch signal) C of boundary B1 is obtained, and by comparison between the clipping signal D and zero cross signal E, position pulse (latch signal) F of boundary B2 is obtained.

The operation processor 10 calculates the height of the plasma S1 in the blood sampling tube 1 on the basis of the measuring result of the signal processor 8, and determines the sedimentation rate of erythrocytes. Specifically, the operation processor 10 calculates the height of the boundaries B2 and B3 from the position pulse (latch signal) F measured and sent out by the signal processor 8, and the sedimentation rate of erythrocytes is determined from this value and the set measuring time (preferably 15 to 20 minutes).

The operation processor 10 also plays the role of the commander to the controller 9 for controlling the pulse motor 4, LED array LD, line sensor LS, etc.

The foregoing description relates to the measuring process of sedimentation rate of erythrocytes for one blood sampling tube 1, but in other seven blood sampling tubes 1, 1 . . . , the sedimentation rate of erythrocytes is measured in the same process. In this case, the blood sampling tubes 1 are identified, although not shown specifically, by reading the ID label adhered to each blood sampling tube 1 by an ID reader 24. This ID label is a strip identifying the owner of the sample, and is glued to the upper position of the blood sampling tube 1. As the ID reader 24, a character reader is used if the ID is composed of characters, or a bar code reader if the ID is composed of bar code.

In the measuring apparatus of sedimentation rate having such constitution, the blood sampling tubes 1, 1, . . . filled with sample are rotated by the turntable 3, relatively to the projecting means 5 and photo detecting means 6, and projection light 14a is projected.

At this time, the ID label on the test container is first read by the ID reader 24, and the blood sampling tube 1 is identified.

By the line sensor LS of the photo detecting means 6 as mentioned above, the quantity of light of the transmitted light 14b passing through the blood sampling tube 1 is detected as an electric signal, and stopping position of the turntable 3 is determined, and the sedimentation rate of erythrocytes is measured.

The result of measurement of sedimentation rate of erythrocytes is displayed in an international standard method by display device or printer not shown in the drawing.

It is not necessary to set all eight blood sampling tubes 1 from the beginning, but they may be set at time intervals or at skipping positions, and anyway they can be identified by means of the ID labels.

In this embodiment, as mentioned above, not only the standard tube 11, but also the capillary tube 12 can be measured by using the capillary holder 13, and the measuring method is same as in the case of the standard tube 11.

EMBODIMENT 2

This embodiment relates to a technique of measuring the serum color in the plasma, aside from the measurement of sedimentation rate of erythrocytes mentioned above, and the measuring apparatus shown in FIG. 6 is used.

This measuring apparatus is same as in embodiment 1, except for the constitution of the projecting means 5. As the light source of the projecting means 5, one kind of LED array is used in embodiment 1, but in this embodiment, two LED arrays differing in wavelength, preferably, a red LED array LD1 and a blue LED array LD2 are used.

In the measuring apparatus of sedimentation rate having such constitution, first, the red LED array LD1 is lit, and the sedimentation rate of erythrocytes is measured, and this measuring process of sedimentation rate of erythrocytes is same as in embodiment 1, and its explanation is omitted.

After the measuring process of sedimentation rate of erythrocytes, the serum color is measured in the following procedure. That is, simultaneously with the end of measuring process of sedimentation rate of erythrocytes, the red LED array LD1 lighting during measurement of sedimentation rate of erythrocytes is kept lit, and the photoelectric conversion output Vb shown in FIG. 5 obtained at this time is A/D converted in the A/D converter 17, and is taken into the operation processor 10.

Next, putting out the red LED array LD1( the blue LED array LD2 is lit, and same as mentioned above, the photoelectric conversion output Vb is A/D converted in the A/D converter 17, and taken into the operation processor 10. These two intake values are compared in the operation processor 10, and the comparison value is calculated.

So far, there is no example of measurement of serum color, and the relation of the measured value and disease is not established, but in future, such measurement of serum color is expected to be useful in diagnosis of disease.

In the foregoing embodiments, for example, the following design changes are possible.

For instance, in the embodiments, although the sedimentation rate of erythrocytes can be measured if the blood sampling tubes 1 are not set in all of eight blood sampling tube holders 2, 2, . . . , but the LED or other pilot lamp may be provided to notice end of measurement or presence or absence of blood sampling tubes 1, 1, . . . corresponding to the blood sampling tube holders 2, 2, . . .

In the embodiments, the scatter boards 15 are provided in the individual blood sampling tube holders 2, 2, . . . , but one scatter board may be disposed between the LED array LD and the inclination holding means.

In the embodiments, the line sensor LS is used as the photo detecting means 6, but an area sensor ES such as CCD area sensor may be used. In such constitution, as compared with the line sensor LS which is capable of detecting light only at one position of the linear sensor orthogonal to the rotating direction of the turntable 3, the area sensor ES can detect light simultaneously at plural positions on the sensor having a specific area in the rotating direction of the turntable 3, so that measurement of higher precision is realized.

That is, if dust sticks to part of the measuring region in the blood sampling tube 1, in the line sensor LS, the light can be detected only at one position as mentioned above, and if the light passing through this contaminated portion is detected, the quantity of received light may be smaller than the true transmitted light quantity, and measuring error or defective measurement may occur. By contrast, in the area sensor ES, since the light can be detected at plural positions on the sensor as an area, if the light passing through the contaminated portion is detected, the light passing through other clean portion is also detected at the same time, so that the true transmitted light quantity can be always detected stably. As a result, if dust sticks to a part of the measuring region in the blood sampling tube 1, regardless of such contamination, measuring error or defective measurement does not occur, so that measuring results of high precision may be obtained.

As described herein, according to the measuring method of sedimentation rate of the invention, since the sample container is held at a specific inclination angle, for example, in the case of measurement of sedimentation rate of erythrocytes, natural convection is formed in the blood, and formation of clots of erythrocytes is promoted, and hence the sedimentation rate is accelerated. As a result, the sedimentation rate of erythrocytes can be measured promptly, and it is very effective for a clinical case requiring an urgent care. Moreover, generation of natural convection by inclination occurs not only in standard tube but also in capillary tube, so that it is effective for measurement of sedimentation rate of erythrocytes in infants.

When measuring the sedimentation rate of erythrocytes at random by using plural test containers, the photoelectric conversion output Va of the transmitted light passing through the space in the test container is A/D converted, and taken into the control means, and when this intake value exceeds a specific value, the pulse motor is reduced in speed, and it is the optimum value when the intake value is equal to the previous intake value or begins to decrease, and the pulse motor is stopped, and the sedimentation rate of erythrocytes is measured, so that the fine capillary, as well as the standard tube, can be stopped precisely at the measuring position.

By using this stopping method, if all test containers are not set, the inclination holding means at the missing position of test container does not stop unnecessarily, but can pass through directly.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A measuring apparatus of sedimentation rate for determining the sedimentation rate of sediments, comprising:

inclination holding means for holding a test container accommodating a liquid sample containing sediments in an inclined state, projecting means for projecting light to said test container, photo detecting means disposed oppositely to said projecting means across said test container, for detecting the light passing through the test container from said projecting means, and converting photoelectrically, light quantity change measuring means for measuring time-course changes of the photo detecting means output, and sedimentation rate calculating means for calculating the sedimentation rate of sediments in the test container on the basis of the result of measurement by the light quantity change measuring means;

wherein said inclination holding means has a structure capable of holding a plurality of test containers differing in shape and size in an inclined state, and the sedimentation rate can be measured in a plurality of test containers differing in shape and size.

2. The measuring apparatus of sedimentation rate of claim 1, wherein said inclination holding means includes detecting means for specifying the type of said plurality of test containers.

3. The measuring apparatus of sedimentation rate of claim 1, wherein a scatter board for scattering light is disposed between said projecting means and inclination holding means.

4. The measuring apparatus of sedimentation rate of claim 1, wherein said projecting means is composed of a line light source, and said photo detecting means is composed of a line sensor.

5. The measuring apparatus of sedimentation rate of claim 1, wherein said projecting means is composed of a line light source, and said photo detecting means is composed of an area sensor.

6. The measuring apparatus of sedimentation rate of claim 1, wherein the inclination angle for holding said test container is set at 15 to 25 degrees.

7. The measuring apparatus of sedimentation rate of claim 1, wherein said liquid sample is blood, and the sedimentation rate of the blood cell layer of erythrocytes as sediments in the blood is measured.

8. A measuring apparatus of sedimentation rate for determining the sedimentation rate of sediments, comprising:

a plurality of inclination holding means for holding a plurality of test containers accommodating liquid samples containing sediments in an inclined state, a turntable on which said plurality of inclination holding means are disposed on the circumference, being supported rotatably about its central axial line, rotation driving means for rotating and driving this turntable, for indexing and stopping one of said test containers so as to be positioned at the measuring position, projecting means for projecting light to said test container positioned at said measuring position, photo detecting means disposed oppositely to said projecting means across this test container, for detecting the light passing through the test container from said projecting means, and converting photoelectrically, light quantity change measuring means for measuring time-course changes of the photo detecting means output, control means for controlling this light quantity change measuring means and said rotation driving means in synchronism, and sedimentation rate calculating means for calculating the sedimentation rate of sediments in the test container on the basis of the result of measurement by the light quantity change measuring means;

wherein said inclination holding means has a structure capable of holding a plurality of test containers differing in shape and size in an inclined state, and the sedimentation rate can be measured in a plurality of test containers differing in shape and size.

9. The measuring apparatus of sedimentation rate of claim 8, wherein when measuring the sedimentation rate after stopping rotation and positioning the turntable during operation of the rotation driving means at a specified rotating speed, the light passing through the space not containing the liquid sample in the test container is received by the photo detecting means, and converted photoelectrically, the output of this photo detecting means is an intake value taken into the control means, and the control means decelerate the rotation driving means when this intake value exceeds a certain value, and the rotation driving means is stopped when the intake value is equal to the previous intake value or begins to decrease, supposing to be an optimum value, the light passing through the test container at the measuring position in this state is detected electrically, the depth of the sediments in the liquid sample is calculated from the time-course changes of this detected value, and the sedimentation rate is determined.

10. The measuring apparatus of sedimentation rate of claim 8, wherein said inclination holding means includes detecting means for specifying the type of said plurality of test containers.

11. The measuring apparatus of sedimentation rate of claim 8, wherein a scatter board for scattering light is disposed between said projecting means and inclination holding means.

12. The measuring apparatus of sedimentation rate of claim 8, wherein said projecting means is composed of a line light source, and said photo detecting means is composed of a line sensor.

13. The measuring apparatus of sedimentation rate of claim 8, wherein said projecting means is composed of a line light source, and said photo detecting means is composed of an area sensor.

14. The measuring apparatus of sedimentation rate of claim 8, wherein the inclination angle for holding said test container is set at 15 to 25 degrees.

15. The measuring apparatus of sedimentation rate of claim 8, wherein said liquid sample is blood, and the sedimentation rate of the blood cell layer of erythrocytes as sediments in the blood is measured.

* * * * *